(12) United States Patent
Tani

(10) Patent No.: US 9,962,473 B2
(45) Date of Patent: May 8, 2018

(54) SURGICAL SUCTION NOZZLE

(76) Inventor: Tohru Tani, Kusatsu (JP)

(*) Notice: Subject to any disclaimer, the term of this patent is extended or adjusted under 35 U.S.C. 154(b) by 472 days.

(21) Appl. No.: 13/376,381

(22) PCT Filed: Jun. 4, 2010

(86) PCT No.: PCT/JP2010/003734
§ 371 (c)(1),
(2), (4) Date: Dec. 5, 2011

(87) PCT Pub. No.: WO2010/143384
PCT Pub. Date: Dec. 16, 2010

(65) Prior Publication Data
US 2012/0078169 A1 Mar. 29, 2012

(30) Foreign Application Priority Data
Jun. 10, 2009 (JP) .................. 2009-139018

(51) Int. Cl.
*A61M 1/00* (2006.01)
*A61M 25/00* (2006.01)

(52) U.S. Cl.
CPC ........ *A61M 1/008* (2013.01); *A61M 25/0082* (2013.01); *A61M 25/0069* (2013.01)

(58) Field of Classification Search
CPC ...... A61M 1/00; A61M 1/008–1/0098; A61M 27/00–27/008
USPC ................ 604/313–316, 540, 544
See application file for complete search history.

(56) References Cited

U.S. PATENT DOCUMENTS

| 4,672,953 A | * | 6/1987 | DiVito .................... 601/162 |
| 5,895,400 A | * | 4/1999 | Abela ..................... 606/159 |
| 6,074,208 A | * | 6/2000 | Mitchell .................. 433/91 |
| 7,036,179 B1 | * | 5/2006 | Weihrauch ............... 15/167.1 |

FOREIGN PATENT DOCUMENTS

| JP | 138449/1989 | 9/1989 |
| JP | 088552/1993 | 12/1993 |
| JP | 06-285155 | 10/1994 |
| JP | 2001-252349 | 9/2001 |
| JP | 2001-252349 A | 9/2001 |

* cited by examiner

Primary Examiner — Jackie Tan-Uyen T Ho
Assistant Examiner — Ned T Heffner
(74) Attorney, Agent, or Firm — Don D. Cha; Hamilton DeSanctis & Cha, LLP

(57) ABSTRACT

The present invention provides a surgical aspiration cannula capable of aspirating a liquid component such as a small amount of blood while keeping an ability to aspirate a large clot such as a blood clot and to sweep them. The present invention relates to a surgical aspiration cannula that comprises a tip opening capable of aspirating a clot such as a blood clot; and an aspiration structure in the front of the tip opening. Due to the aspiration structure, the liquid component such as a small amount of blood can be aspirated. Further, even when the tip opening is pressed against the vicinity of an organ, the aspiration structure interposed between an aspiration port and a surface of the organ prevents clogging of the cannula or damage to the organ. In addition, in a case of bleeding in a surgical site, the blood is aspirated while controlling the bleeding by pressurizing a bleeding site, thereby providing a clear view and enabling a hemostatic site to be treated.

16 Claims, 7 Drawing Sheets

SURGICAL SUCTION NOZZLE

TECHNICAL FIELD

The present invention relates to a surgical aspiration cannula that aspirates and removes blood, exuding body fluid, exfoliated small tissues and cleansing liquid during a surgical operation.

BACKGROUND ART

Aspiration of blood, cleansing liquid, and body fluid during a surgical operation is necessary to ensure a clear view of surgical site and safety and precision of the surgical operation. In general, a surgical aspiration tube includes an elongated cylindrical aspiration tube that is connected to an aspiration device by a central pipe. A surgical aspiration tube is used to remove blood and cleansing liquid during a surgical procedure. There are disposable or reusable surgical aspiration tubes, and most of the surgical aspiration tubes have a tip opening that is several millimeters in size at a tip end. Further, some surgical aspiration tubes have a hole on a side wall, or have an outside cap with a side hole to prevent aspirating tissues. Thus, the surgical aspiration tubes are devised so as to aspirate liquid components effectively.

The same cannula may be provided with a water injection valve at some midpoint thereof so as to allow cleaning of the surgical site or it may also have other components to allow electrical coagulation of the surgical site.

Further, in a brain surgery, the aspiration is conducted through a small cotton sheet so that brain tissues are not damaged by aspiration. In a laparoscopic surgical operation, the aspiration is achieved through a small gauze that is inserted into the aspiration tube. When a blood vessel bursts during a surgical procedure, a large amount of blood flow makes it difficult to locate the area of bleeding. In such instances it is necessary to constrict the bleeding point to stop or slow the blood flow while simultaneously maintaining aspiration. However, the use of conventional aspiration tube accelerates the bleeding, and can even cause enlargement of the blood vessel rupture.

If an aspiration port is limited to the tip opening, a soft organ, such as a greater omentum, and a blood clot can block the tip opening and hinder aspiration. Therefore, in an abdominal surgical operation, the aspiration is conducted with an outer cylinder having a large number of minute holes on a side wall (Patent Literature 1). Even then, the greater omentum and the like are often aspirated into the minute holes making it impossible to conduct effective aspiration and may also damage the tissue. Further, when the side holes are open, air enters from the side, and hence, a small amount of remaining fluid and blood cannot be removed. Therefore, there is a need for a method for removing liquid components such as a small amount of remaining accumulated fluid and a small amount of blood covering the surface of an organ without damaging the organ.

Typically, a laparoscopic surgical operation is performed by injecting carbon dioxide into the abdominal cavity. If the side hole of the aspiration tube is open, a great amount of pressurized carbon dioxide is removed due to aspiration, thereby eliminating the effect of gas enlarging the abdominal cavity. As a result, a clear view cannot be obtained. Further, in the laparoscopic surgical operation, it is difficult to remove the entire blood using a gauze. Further, in the laparoscopic surgical operation, it is necessary to perform the surgical operation without replacing the cannula frequently. Thus, there is a demand for means for effectively removing liquid components such as a small amount of remaining blood and a small amount of body fluid remaining on the surface of an organ without damaging the organ and aspirating pressurized gas during the laparoscopic surgical operation.

In cases where there is further bleeding in a surgical site, it is necessary to maintain a viewable hemostatic site by pressurizing the bleeding site while aspirating and controlling bleeding. Therefore, there is also a demand for means for simultaneously aspirating and controlling bleeding.

CITATION LIST

Patent Literature

Patent Literature 1: Japanese Utility Model Application Laid-open No. Hei 7-22743

SUMMARY OF THE INVENTION

Technical Problem

The present invention provides a surgical aspiration cannula capable of aspirating a liquid component such as a small amount of blood without damaging an organ while maintaining the ability to aspirate a large clot such as a blood clot.

Solution to Problem

The inventor of the present invention has intensively studied so as to solve the above-mentioned problem, and found that the problem can be solved by a cannula having a particular aspiration structure to achieve the objectives of the present invention.

That is, the present invention includes the following items:

1. A surgical aspiration cannula, including: a tip opening capable of aspirating a clot such as a blood clot; and a flexible aspiration structure extending in an axial front direction of a cannula from the tip opening.

2. A surgical aspiration cannula according to the above-mentioned item 1, in which the flexible aspiration structure is arranged at a tip opening tube wall of the surgical aspiration cannula.

3. A surgical aspiration cannula according to the above-mentioned item 1 or 2, in which the flexible aspiration structure is formed of a bristle and/or a protrusion.

4. A surgical aspiration cannula according to any one of the above-mentioned items 1 to 3, in which the flexible aspiration structure includes a bristle structure including a plurality of bristles.

5. A surgical aspiration cannula according to any one of the above-mentioned items 1 to 4, in which the flexible aspiration structure is arranged along the tip opening tube wall.

6. A surgical aspiration cannula according to any one of the above-mentioned items 1 to 5, in which the flexible aspiration structure includes an aspiration structure formed by packing a plurality of bristles and/or protrusions, and in a cross-section of the tip opening of the surgical aspiration cannula, a ratio of a cross-sectional area of the aspiration structure to a cross-sectional area of the tip opening of the cannula is 5% to 60%.

7. A surgical aspiration cannula according to any one of the above-mentioned items 1 to 6, in which the flexible aspiration structure includes a disposable aspiration structure connectable to and removable from an aspiration cannula body.

8. A surgical aspiration cannula according to any one of the above-mentioned items 1 to 7, in which a length from the tip opening to a tip end of the flexible aspiration structure is 0.2 times to 10 times a diameter of the tip opening.

9. A surgical aspiration cannula tip end unit, including an aspiration structure, the surgical aspiration cannula tip end unit being capable of forming the surgical aspiration cannula according to items 1 to 8 above by being connected to the aspiration cannula body.

10. A surgical aspiration cannula tip end unit according to the above-mentioned item 9, including an aspiration structure and a cannula tip opening, in which the aspiration structure is arranged at a cannula tip opening tube wall.

11. A surgical treatment tool, including the surgical aspiration cannula according to any one of items 1 to 8 above; and coagulation incision means and/or cleansing means.

Advantageous Effects of Invention

The surgical cannula of the present invention is capable of collecting and aspirating liquid components such as a small amount of blood and body fluid through a capillary action without clogging the orifice while keeping the ability to aspirate a large clot such as a blood clot during an open surgical operation or laparoscopic surgical operation. Further, the surgical cannula is capable of sweeping as in a broom. Therefore, even a blood clot on the surface of an organ can be removed as if the blood clot was wiped away while the surface is being cleansed so that the original color of the organ can be recognized.

Further, even when the surgical cannula is pressed against an organ, the aspiration structure interposed between the aspiration port and the surface of the organ hinders clogging, and thus, the effective aspiration of fluid can be conducted smoothly and rapidly.

Further, the bleeding can be controlled by pressurizing a bleeding site with the aspiration structure. Simultaneously, blood can be aspirated so that the blood is not accumulated, and hence, a bleeding point becomes clear and an effective hemostasis can be achieved.

In brain surgery, it is a contraindication to damage the brain tissue. The aspiration cannula of the invention is capable of collecting blood and cleansing liquid in the aspiration structure through a capillary action and it is also capable of operating as a broom and it can aspirate without bringing the aspiration cannula in contact with the brain tissue, and it is further capable of controlling a bleeding site. Therefore, the surgical aspiration cannula of the invention is particularly effective in aspiration during a brain surgery.

DESCRIPTION OF EMBODIMENTS

Figure 1:
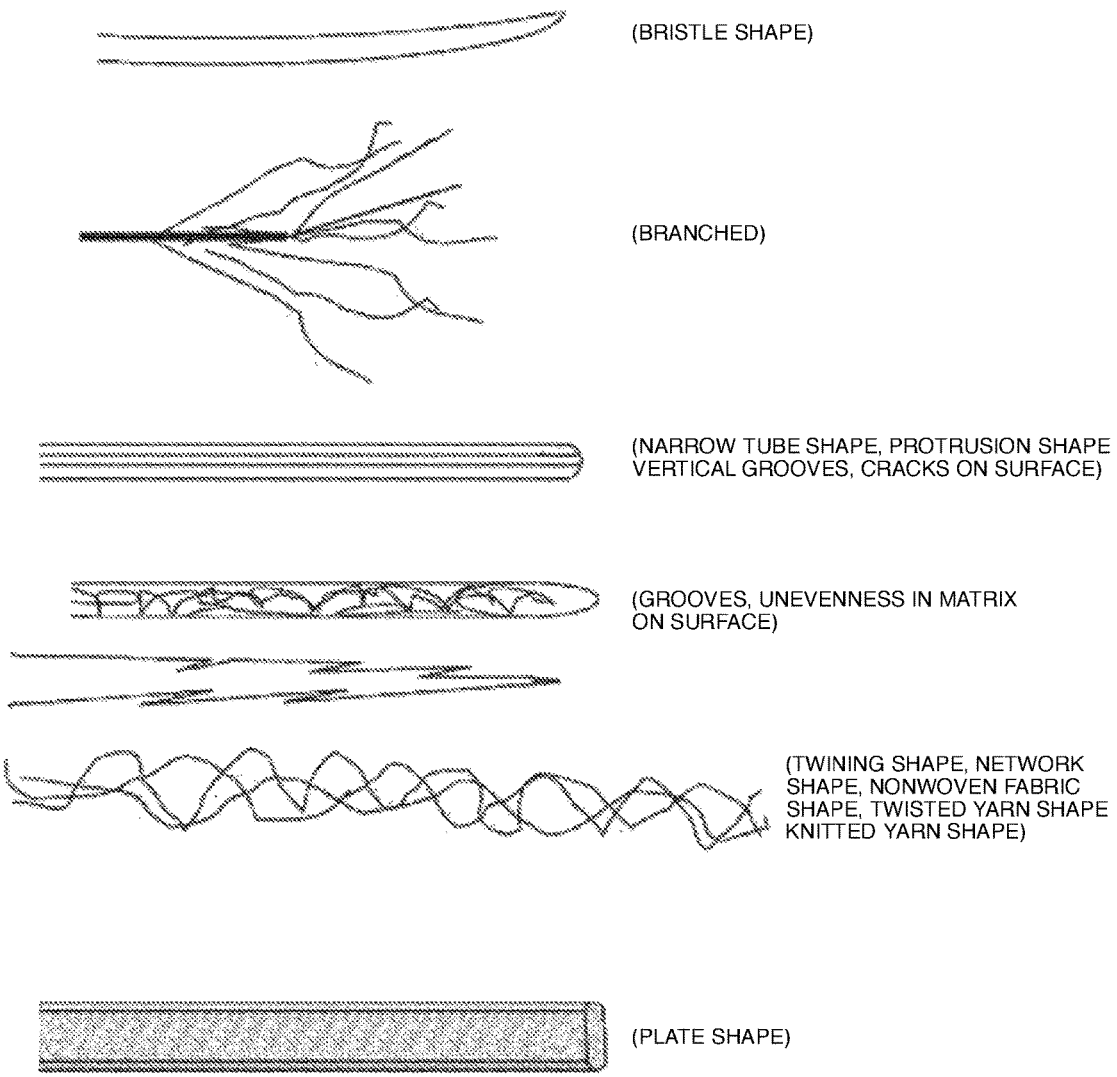
FIG. 1 A view illustrating shapes and states of a surface of a bristle or a protrusion constituting an aspiration structure according to the present invention.

The present invention relates to a surgical aspiration cannula that comprises: a tip opening capable of aspirating a clot such as a blood clot; and a flexible aspiration structure extending in an axial front direction of a cannula from the tip opening.

Herein, the tip opening refers to an opening of a tip end portion of the cannula that aspirates blood, body fluid, and cleansing liquid used during a surgical operation. The axial front direction of the cannula from the tip opening refers to a further front direction from the vicinity of the tip opening. The surgical aspiration cannula of the present invention has a flexible aspiration structure that extends in the axial front direction of the cannula from the tip opening, and the tip opening maintains an ability to aspirate a clot such as a blood clot.

The aspiration structure according to the present invention is a flexible structure that is formed of a plurality of bristles and/or protrusions. Examples of the aspiration structure include a bristle structure formed of a plurality of bristles, a protrusion structure formed of a plurality of flexible protrusions, and a structure formed of a plurality of bristles and a plurality of protrusions.

The aspiration structure used in the present invention causes a capillary action. The bristles and protrusions are not so hard as to damage an organ, have elasticity and resilience, return to the original shapes even after being pressurized, are not too soft, and have elasticity and hardness to such a degree that the bristles and protrusions are not aspirated by an aspiration port. It is preferred that the aspiration structure has a function of alleviating the contact between a tissue and a cannula opening during a surgical operation and simultaneously achieve a sufficient aspiration. The aspiration structure can aspirate liquid components such as a small amount of blood through a capillary action of the aspiration structure and can simultaneously perform an operation of sweeping like a broom. On the other hand, when the aspiration structure is dense and has elasticity, the aspiration structure can control the bleeding by pressurizing a point at a time of bleeding, and can simultaneously aspirate blood in such a manner that the blood is not accumulated. Further, even if the tip opening is pressed against the vicinity of an organ, the aspiration structure is interposed between the aspiration port and the surface of the organ to prevent clogging of the aspiration port by the organ or cause damage to the organ.

It is preferred that the aspiration structure of the cannula of the present invention be shaped so as not to damage an organ, have softness and elasticity, and have a tip end which is thin and bent smoothly. Further, in order to allow the cannula to proceed to a target site in the laparoscopic surgical operation, it is preferred that the tip end of the aspiration structure as a whole be as thin as possible.

The bristle and protrusion may have one root and be branched at a periphery. Further, the bristle and protrusion may have a narrow tube shape, a twining shape, a network shape, a twisted yarn shape, a knitted yarn shape, a nonwoven fabric shape, or a plate shape.

Further, although the surface of the bristle and the protrusion may be smooth, the surface of the bristle and the protrusion may be provided with unevenness or grooves so as to cause a capillary action easily. For example, the bristle and the protrusion may be provided with vertical grooves, cracks, or grooves in a matrix.

It is preferred that the shape of the bristle or the protrusion close to a tip end thereof be tapered. Further, it is suitable that the tip end be rounded.

The cross-section of the bristle may be circular or non-circular without any limit, and the diameter of the cross-section in the case where the bristle is circular is preferably 0.001 to 1 mm, more preferably 0.005 to 0.5 mm, still more preferably 0.01 to 0.2 mm, most preferably 0.05 to 0.15 mm. The suitable thickness of the bristle varies depending upon an organ for which the bristle is used and a purpose of use.

The cross-section of the protrusion may be circular or non-circular without any limit, and the diameter of the cross-section in the case where the protrusion is circular is preferably 0.1 to 1 mm, more preferably 0.3 to 0.8 mm. In the case where the protrusion is oval, the preferred long diameter thereof is 0.1 to 1 mm, and the preferred short diameter thereof is 0.001 to 0.5 mm. The suitable thickness of the protrusion varies depending upon a material to be used, an organ for which the protrusion is used, and a purpose of use.

In the case of a thick bristle or protrusion, it is preferred that the bristle or protrusion be devised so as to be provided with unevenness or grooves on the surface or so as to have a knitted yarn shape or a twisted yarn shape.

Regarding the length of the aspiration structure of the cannula of the present invention, the length from the tip opening to the tip end of the aspiration structure is preferably 0.2 to 10 times, more preferably 0.5 to 5 times the diameter of the tip opening. That length is preferably 2 mm to 30 mm, more preferably 2 mm to 20 mm, still more preferably 5 mm to 15 mm. If the length is smaller than the length that is 0.2 times the diameter of the tip opening, the effect of protecting a tissue and the like is insufficient, and the effect of removing a small amount of liquid components in a narrow portion is insufficient. If the length is larger than the length that is 10 times the diameter of the tip opening, the effect of aspiration is degraded, with the result that the aspiration structure hinders the surgical operation. Although the aspiration structure of a small length is unsuitable for the protection of a tissue, it has an advantage of keeping the aspiration force, and the suitable length and hardness vary depending upon an organ for which the aspiration structure is used and a purpose of use.

It is preferred that the number and density of bristles or protrusions constituting the aspiration structure of the cannula of the present invention be set to form such an assembly as to exhibit a sufficient capillary action. Further, it is preferred that the number and density of bristles or protrusions be set to form such an assembly as to prevent adhesion between an organ and the cannula or cause damage to the organ due to adhesion by aspiration. Further, it is preferred that the number and density of bristles or protrusions be set to form such an assembly as to control bleeding.

The surgical aspiration cannula of the invention of the present application has a tip opening capable of aspirating a clot such as a blood clot. Having a tip opening capable of aspirating a clot such as a blood clot refers to having an opening with such a size as to aspirate not only liquid blood, cleansing liquid, and the like, but also a clot such as a blood clot.

In the surgical aspiration cannula of a preferred embodiment of the invention, the aspiration structure is arranged on a tip opening tube wall of the aspiration cannula. Examples of the arrangement position include an inner side, a tip end, and an outer side of the tip opening tube wall.

In the surgical aspiration cannula of one embodiment of the invention, the aspiration structure is arranged along the tip opening tube wall. The arrangement position and arrangement method are not limited. For example, the aspiration structure may be arranged at the tip end of the opening tube wall, or may be arranged along the outer side or inner side of the tube wall.

The aspiration structure is arranged along a part or all of the tip opening tube wall of the cannula. Depending upon the purpose, the bristles or protrusions are arranged along 5% to 100%, preferably 10% to 100%, more preferably 15% to 100% of the circumference of the opening tube wall. Depending upon an organ and a purpose of use, the bristles or protrusions are arranged along preferably 10% to 80%, more preferably 15% to 60%, still more preferably 20% to 50% of the circumference.

The suitable arrangement ratio of the aspiration structure varies depending upon an organ and the purpose of use. In the case of brain surgery in which it is a contraindication to damage an organ by aspiration and an aspiration amount is small, the aspiration structure may be arranged around the opening. In the case where it is required to aspirate a great amount of liquid components, the aspiration structure may be arranged so as to inhibit the adsorption with respect to an organ even if a capillary action may not be realized. In the case where the aspiration structure is arranged partially, it is suitable that the aspiration structure be arranged along the opening tube wall on a lower side (side on which there is a possibility of the contact with a tissue and the like) of the cannula. If the aspiration structure is arranged along 5% or less of the circumference, it becomes difficult to achieve a desired aspiration, protect a tissue, and achieve hemostasis.

In the case where the bristles or protrusions are arranged along the tip opening tube wall, the bristles or protrusions may be arranged one by one, or may be arranged on the basis of a plurality of the bristles or protrusions. Further, the bristles or protrusions may be arranged in one, two, three, or more lines.

In another embodiment of the present invention, the aspiration structure formed by packing a plurality of bristles and/or protrusions is arranged in an inner portion of the cannula, an outer portion thereof, or at a tip end of the tube wall. Regardless of any particular arrangement, the aspiration structure is suitably arranged on a lower side (side on which there is a possibility of the contact with a tissue and the like) of the cannula.

In the case where the aspiration structure is formed by packing a plurality of bristles and/or protrusions in an inner portion of the tip opening, the ratio of the cross-sectional area of the aspiration structure with respect to the cross-sectional area of the tip opening of the cannula is preferably 5% to 60%, more preferably 10% to 60%, still more preferably 15% to 45%, yet more preferably 20% to 40%. By setting the cross-sectional area of the aspiration structure to be 60% or less, an opening can be ensured, which is capable of aspirating a clot such as a blood clot.

In the case where the aspiration structure is formed by packing a plurality of bristles and/or protrusions in an outer portion of the cannula or arranged at a tip end of the tube wall, the tip opening is ensured. It is preferred that the amount of aspiration structure be equal to that of the aspiration structure that is arranged in an inner portion of the cannula.

In the case where the aspiration structure has a configuration in which a plurality of bristles and/or protrusions are packed, the specific number of the bristles and/or protrusions is about 10 to 500. The number can vary depending upon the thickness and shape of the bristles and/or protrusions, a purpose of use, and an organ in a surgical site.

The material for the cannula of the present invention is not particularly limited, and a generally any conventional material may be used. For example, a metal material such as stainless steel, a titanium alloy, duralumin, or aluminum or a resin material such as a nylon resin, an ABS resin, a polycarbonate resin, or saturated propylene may be used. A composite material of a metal material and a resin material may also be used.

It is preferred that the material for bristles or protrusions of the aspiration structure of the present invention be soft and do not damage an organ. However, there is no particular limitation as to the material, as long as the material has flexibility and elasticity, bends smoothly, and has resilience. For example, natural fibers, natural hair, artificial fibers, artificial hair, plastic, nylon, vinylon, saturated propylene, and the like can be used. Those which are generally used for a toothbrush may be used.

In order to prevent the aspiration structure from coming off from the cannula, the material for the cannula may be set to be the same as that for the aspiration structure. It is preferred that the aspiration structure can be molded integrally with the tube wall of the cannula.

The aspiration structure can be formed of a thin hollow yarn. In the case where the aspiration structure is arranged in an inner portion of the cannula, liquid components such as blood and body fluid can be aspirated by aspiration through the cannula, and hence, the hollow yarn may or may not be connected to a central aspiration cleansing device. The effect of aspirating liquid components is further enhanced by the ability to aspirate through the tip opening and the hollow yarn. It is preferred that the hollow yarn be connected to the central aspiration cleansing device, and in this case, it is preferred that the aspiration be divided into aspiration by the aspiration structure and aspiration by the tip opening. By dividing the aspiration, the operation and adjustment of aspiration and cleansing can be performed individually in the hollow yarn portion and the tip opening.

It is preferred that the surgical aspiration cannula of the present invention does not have a hole on the side wall of the cannula for aspirating a small amount of fluid. If the side hole is open, air enters from the side, which makes it difficult to aspirate a small amount of remaining fluid and blood. Particularly in the laparoscopic surgical operation, if the side hole is open, air and the like enter from the side to eliminate the effect of enlarging an abdominal cavity by the gas pressurization.

A thick aspiration tube having a hole on a side wall is preferred for cleansing (about 1 to 10 L are used) during the abdominal surgical operation. In this case, it is sufficient as long as the aspiration tube does not adhere to a tissue, and preferably, the aspiration structure is provided on the outside of the side hole.

In some embodiments, the aspiration structure is fixed to the tip opening of the cannula or the periphery thereof. Although there is no particular limitation to the fixing method, the aspiration structure can be fixed by weld joining, adhesion joining, integral molding, bondage, or the like.

The aspiration structure, or the tip opening or the periphery thereof to which the aspiration structure is fixed may be removable from the aspiration cannula body.

Because it is difficult to cleanse and disinfect the aspiration structure of the invention after the use, it is preferred that the aspiration structure be disposable. If the aspiration cannula body is reusable, only the aspiration structure may be disposable. The tip opening of the aspiration cannula may also be disposable. Further, the tip opening and the aspiration structure may be molded integrally.

At the time of use, the aspiration structure is connected to the aspiration cannula body. It is preferred that the aspiration structure be attached to the aspiration cannula by one-touch attachment through a cassette-shaped attachment unit. The aspiration structure may be attached to the aspiration cannula through a screw, fitting, an elastic band, or the like. The aspiration cannula itself may be disposable.

The present invention also includes a surgical aspiration cannula including a reusable aspiration cannula and a disposable aspiration structure attached removably to the tip end of the aspiration cannula.

The cannula of the present invention may have an outer cylinder. The outer cylinder is suitable for allowing the cannula of the present invention to proceed to a target site during the laparoscopic surgical operation. Further, the cannula of the present invention may have functions other than aspiration. Examples of the functions include a cleansing function and a coagulation ability with an electromagnetic wave. For example, in the case where the surgical aspiration cannula of the invention is connected to cleansing means, the surgical aspiration cannula has a cleansing function. In the case where the surgical aspiration cannula is connected to coagulation incision means, the coagulation incision means can be extended to a surgical site from an inner portion or an outer portion of the cannula of the present invention.

Further, the surgical aspiration cannula of the present invention can be used together with the coagulation incision means and/or cleansing means for a living tissue. Further, the present invention provides a surgical treatment tool in which the surgical aspiration cannula, and the coagulation incision means and/or the cleansing means are integrated. Examples of the tool include a surgical treatment tool in which the coagulation incision means and/or the cleansing means are provided outside of the aspiration cannula of the present invention, and a surgical treatment tool including the aspiration cannula of the present invention, and the coagulation incision means and/or the cleansing means in the outer cylinder. The treatment tools provided with these means enable a surgical operation to be performed precisely and easily. An example of the coagulation incision means is means for cutting a tissue after coagulating the tissue with an electromagnetic wave.

The present invention further relates to a surgical aspiration cannula tip end unit including an aspiration structure connectable to the surgical aspiration cannula body. The surgical aspiration cannula tip end unit includes a cannula connecting portion and an aspiration structure. The surgical aspiration cannula tip end unit may further include a surgical aspiration cannula tip opening. It is preferred that the tip opening and the aspiration structure be made of the same material or be molded integrally.

It is preferred that the aspiration cannula tip end unit be disposable. When the aspiration cannula tip end unit of the present invention is connected to the surgical aspiration cannula body, the aspiration cannula tip end unit includes a surgical structure capable of forming the aspiration cannula of the present invention.

The tip end unit can be connected to the surgical aspiration cannula body through a screw, fitting, an elastic band, or the like. It is preferred that the tip end unit be connected to the surgical aspiration cannula body by one-touch attachment through a cassette-shaped attachment unit or an elastic band.

Hereinafter, examples of the present invention are described with reference to the drawings.

Example 1

Figure 2:
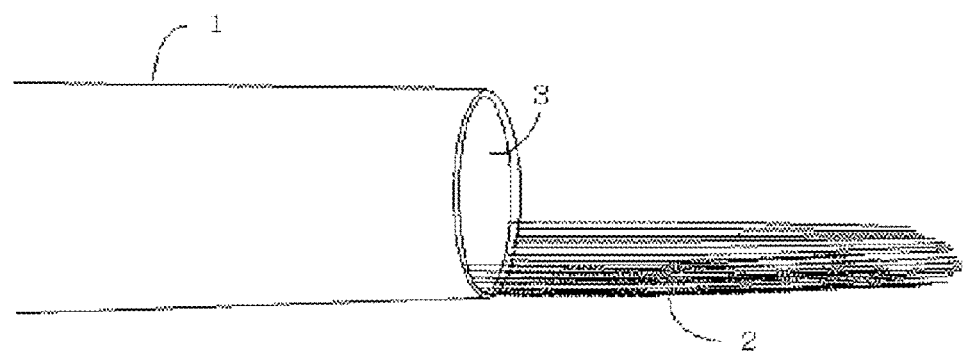
FIG. 2 A perspective view of a tip end of a surgical aspiration cannula according to Example 1.

FIG. 2 illustrates a surgical aspiration cannula of this example. The surgical aspiration cannula of this example includes a cylindrical aspiration cannula body portion 1 and an aspiration structure 2 formed of bristles arranged at the tip end of the aspiration cannula body portion 1. The aspiration structure was integrally molded with a 30% portion of the circumference of a tip opening 3 of a cannula. The length from the opening of the cannula to the tip end of the aspiration structure is 2.2 times (1.1 cm) the outer diameter of the tip opening. The tip end portion of the aspiration structure is thinned as a whole. The bristles are made of a nylon material, and the thickness thereof is 100 µm in diameter. The vicinity of the tip end of the bristles is tapered, and the tip end portion has a semi-spherical shape. When the cannula having the aspiration structure was lightly pressed against the surface of an organ of a dog and liquid components were aspirated as if the liquid components were swept, a small amount of the liquid components on the surface of the organ was aspirated without the surface of the organ adhering to the cannula. Further, when the cannula was pressed against the small amount of the liquid components remaining in a small dent and the liquid components were aspirated, the small amount of the liquid components was aspirated without the cannula adhering to the organ.

Example 2

Figure 3:
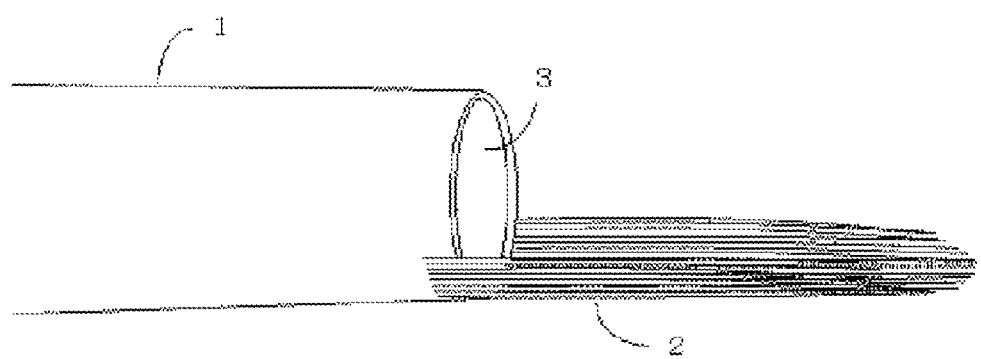
FIG. 3 A perspective view of a tip end of a surgical aspiration cannula according to Example 2.

FIG. 3 illustrates a surgical aspiration cannula of this example. The surgical aspiration cannula has the same shape and material as those of the aspiration cannula of Example 1, except that the surgical aspiration cannula is obtained by weld-joining the aspiration structure to an outer portion of the tip opening tube wall of the cannula. When the effect of the cannula having this aspiration structure was checked in the same way as in Example 1, the satisfactory results were obtained in the same way as in Example 1.

Example 3

Figure 4:
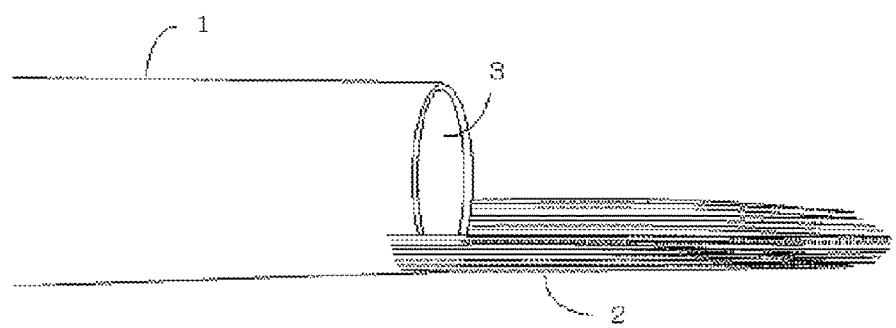
FIG. 4 A perspective view of a tip end of a surgical aspiration cannula according to Example 3.
Figure 5:
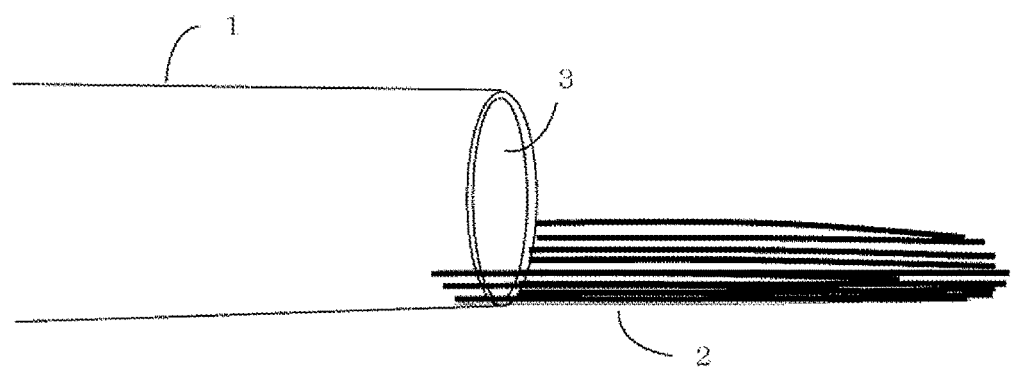
FIG. 5 A perspective view of a tip end of a surgical aspiration cannula according to one embodiment of the present invention.
Figure 6:
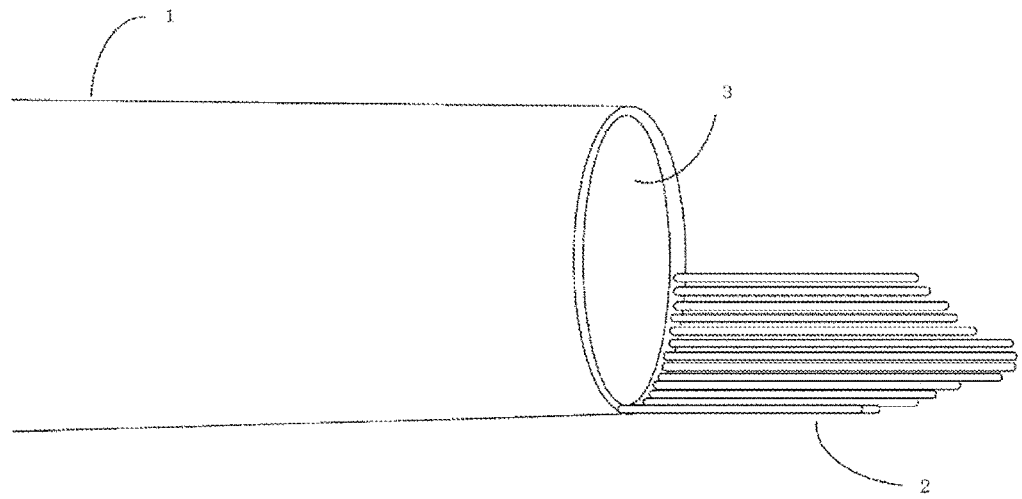
FIG. 6 A perspective view of a tip end of a surgical aspiration cannula according to another embodiment of the present invention.
Figure 7:
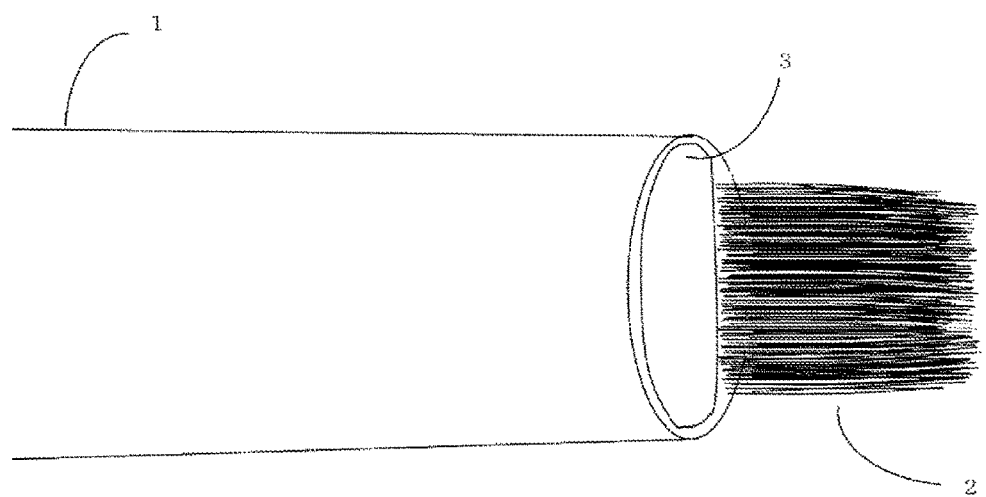
FIG. 7 A perspective view of a tip end of a surgical aspiration cannula according to a further embodiment of the present invention.
Figure 8:
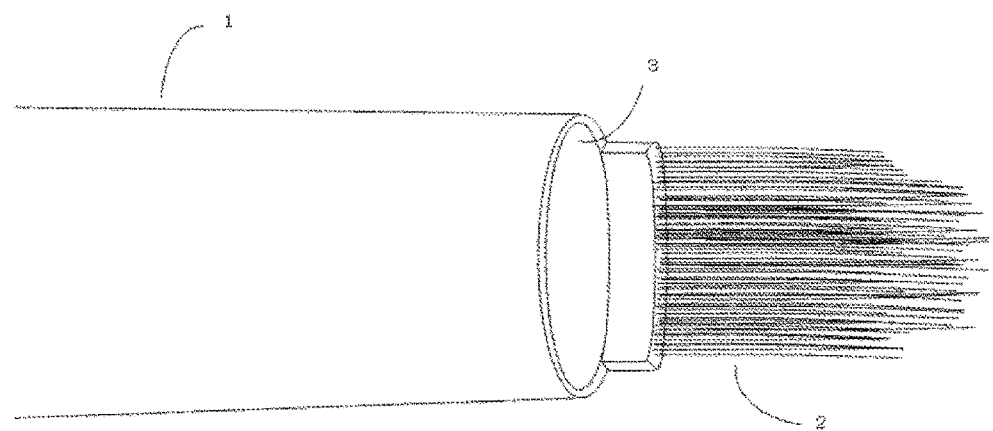
FIG. 8 A perspective view of a tip end of a surgical aspiration cannula according to a still further embodiment of the present invention.
Figure 9:
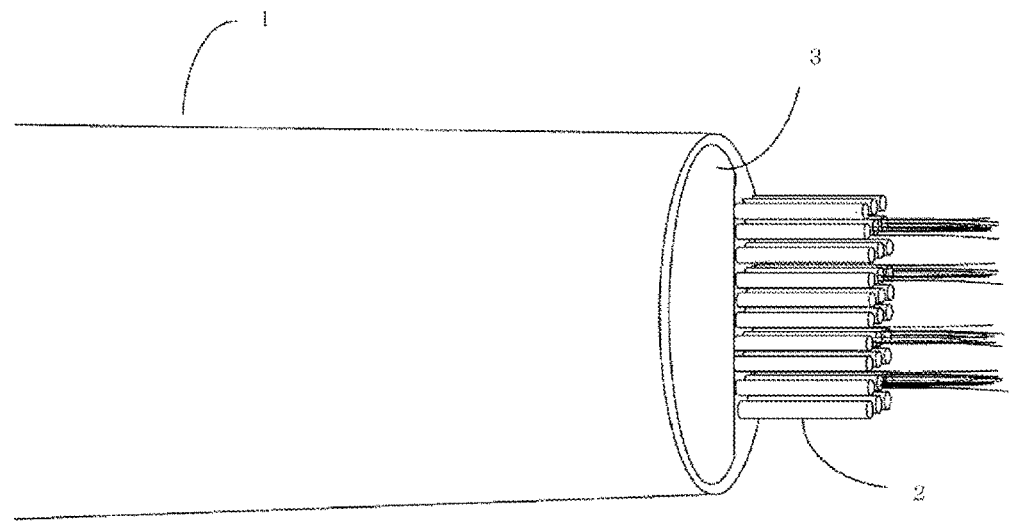
FIG. 9 A perspective view of a tip end of a surgical aspiration cannula according to a yet further embodiment of the present invention.
Figure 10:
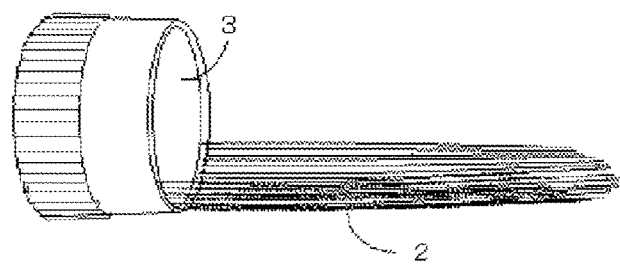
FIG. 10 A perspective view of a tip end unit for a surgical aspiration cannula according to one embodiment of the present invention.
Figure 11:
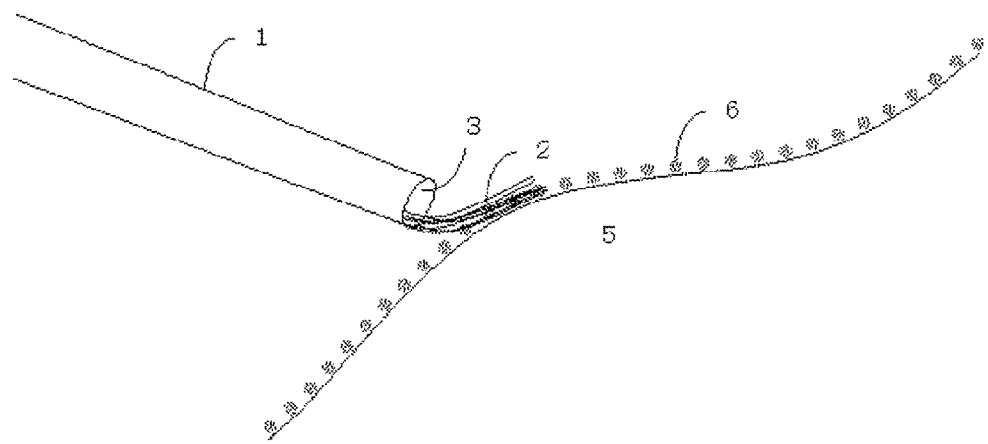
FIG. 11 A use example of the surgical aspiration cannula of the present invention, illustrating that liquid components such as a small amount of blood and body fluid remaining on a surface of an organ can also be aspirated.
Figure 12:
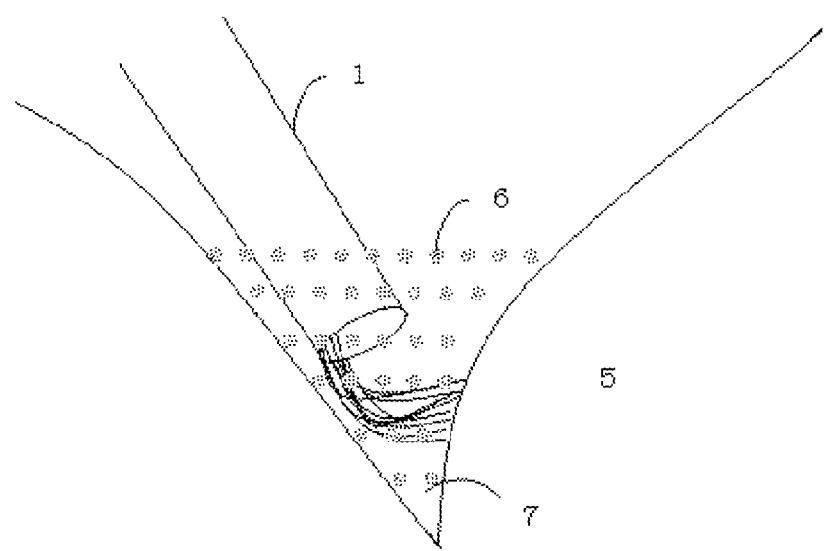
FIG. 12 A use example of the surgical aspiration cannula of the present invention, illustrating that liquid components such as a small amount of blood and body fluid remaining at a narrow site can be aspirated completely.

FIG. 4 illustrates a surgical aspiration cannula of this example. The surgical aspiration cannula of this example includes a cylindrical aspiration cannula body portion 1. An aspiration structure 2 is present in a lower portion inside the aspiration cannula body and the aspiration structure extends forward from inside of a tip opening 3. The aspiration structure is formed of a hollow yarn 4, and aspiration is divided into aspiration by the tip opening and aspiration by the hollow yarn. An aspiration passage by the tip opening and the aspiration structure formed of the hollow yarn are separated from each other by a partition wall 8 inside the cannula. The hollow yarn is connected to a central aspiration cleansing device and is capable of aspirating liquid components such as blood and body fluid independently from the tip opening. If the hollow yarn is stuck, the hollow yarn is capable of aspirating the liquid components after cleansing. The hollow yarn is fixed to an inner side of the aspiration cannula body through adhesion joining. The hollow yarn occupies 35% of the cross-sectional area of the tip opening. The length from the tip opening to the tip end of the hollow yarn is twice (1.0 cm) the outer diameter of the tip opening. The bristles are made of a nylon material, and the thickness thereof is 500 µm in diameter and 400 µm in inner diameter. When the cannula having the aspiration structure was pressed against the surface of an organ of a dog and liquid components were aspirated, the liquid components were aspirated without the surface of the organ adhering to the cannula. Further, when the small amount of the liquid components remaining in a small dent was aspirated, the small amount of the liquid components was aspirated without damaging the organ.

FIGURE LEGENDS

1 cylindrical aspiration cannula body
2 aspiration structure
3 tip opening
4 hollow yarn
5 organ
6 liquid component such as blood and body fluid
7 narrow portion in surgical site
8 partition wall inside cannula

The invention claimed is:
1. A surgical aspiration cannula, comprising:
   a tip opening that is capable of aspirating a clot; and
   a flexible aspiration structure comprising a plurality of extended bristles arranged in a coaxial direction of a cannula from the tip opening and having capillary action.
2. The surgical aspiration cannula according to claim 1, wherein said flexible aspiration structure is located at a tube wall of said tip opening.
3. The surgical aspiration cannula according to claim 1, wherein said flexible aspiration structure is formed of an elastic bristle, a protrusion, or a combination thereof.
4. The surgical aspiration cannula according to claim 1, wherein said flexible aspiration structure is arranged along said tip opening tube wall.
5. The surgical aspiration cannula according to claim 1, wherein said flexible aspiration structure comprises a disposable aspiration structure that is removably attached to an aspiration cannula body.
6. The surgical aspiration cannula according to claim 1, wherein a length from said tip opening to a tip end of said flexible aspiration structure ranges from 0.2 times to 10 times a diameter of said tip opening.
7. A surgical tool, comprising:
   the surgical aspiration cannula of claim 1; and
   a coagulation incision means, a coagulation cleansing means, or a combination thereof.

8. The surgical aspiration cannula according to claim 1, wherein 15% to 60% of the circumference of said tip opening tube wall comprises said flexible aspiration structure.

9. The surgical aspiration cannula according to claim 1, wherein said flexible aspiration structure comprises a plurality of bristles, protrusions, or a combination thereof located in an inner portion of said tip opening and in a cross-section of said tip opening of said surgical aspiration cannula, and wherein a ratio of a cross-sectional area of said flexible aspiration structure to a cross-sectional area of said tip opening of said cannula ranges from 5% to 60%.

10. The surgical aspiration cannula according to claim 1, wherein said flexible aspiration structure is capable of being used to sweep a surgical site and inhibits adsorption to an organ.

11. The surgical aspiration cannula according to claim 1, wherein said flexible aspiration structure comprises a bristle structure.

12. The surgical aspiration cannula according to claim 11, wherein said flexible aspiration structure comprises a plurality of said bristles.

13. The surgical aspiration cannula according to claim 1, wherein said flexible aspiration structure comprises an aspiration structure formed by packing a plurality of bristles, protrusions, or a combination thereof and in a cross-section of said tip opening of said surgical aspiration cannula.

14. The surgical aspiration cannula according to claim 13, wherein a ratio of a cross-sectional area of said flexible aspiration structure to a cross-sectional area of said tip opening of said cannula ranges from 5% to 60%.

15. A surgical aspiration cannula tip end unit, comprising an aspiration structure, wherein when said surgical aspiration cannula tip end unit is connected to an aspiration cannula body the surgical aspiration cannula of claim 1 is formed.

16. The surgical aspiration cannula tip end unit of claim 15 further comprising an aspiration structure and a cannula tip opening, wherein said aspiration structure is located at a tube wall of said cannula tip opening.

* * * * *